United States Patent
Schwab et al.

(10) Patent No.: US 12,169,192 B2
(45) Date of Patent: Dec. 17, 2024

(54) METHODS OF IDENTIFYING A HYDROCARBON FUEL

(71) Applicant: Afton Chemical Corporation, Richmond, VA (US)

(72) Inventors: Scott D. Schwab, Richmond, VA (US); Dana Anderson, Williamsburg, VA (US)

(73) Assignee: AFTON CHEMICAL CORPORATION, Richmond, VA (US)

(*) Notice: Subject to any disclaimer, the term of this patent is extended or adjusted under 35 U.S.C. 154(b) by 160 days.

(21) Appl. No.: 17/087,127

(22) Filed: Nov. 2, 2020

(65) Prior Publication Data

US 2022/0136968 A1    May 5, 2022

(51) Int. Cl.
| | |
|---|---|
| G01N 33/28 | (2006.01) |
| C10L 1/00 | (2006.01) |
| G01N 1/40 | (2006.01) |
| G01N 21/64 | (2006.01) |
| C09B 11/08 | (2006.01) |
| C09B 11/24 | (2006.01) |

(52) U.S. Cl.
CPC .......... *G01N 33/2882* (2013.01); *C10L 1/003* (2013.01); *G01N 1/4055* (2013.01); *G01N 21/64* (2013.01); *C09B 11/08* (2013.01); *C09B 11/24* (2013.01); *C10L 2200/0423* (2013.01); *C10L 2230/16* (2013.01); *G01N 2001/4061* (2013.01)

(58) Field of Classification Search
CPC ........ G01N 33/2882; G01N 2001/4061; C10L 1/003; C10L 2200/0423; C10L 2230/16; C09B 11/24; C09B 11/245; C09B 11/08
See application file for complete search history.

(56) References Cited

U.S. PATENT DOCUMENTS

| | | | |
|---|---|---|---|
| 2,425,755 A | 8/1947 | Roberts et al. | |
| 2,425,845 A | 8/1947 | Toussaint et al. | |
| 2,448,664 A | 9/1948 | Fife et al. | |
| 2,457,139 A | 12/1948 | Fife et al. | |
| 2,475,755 A | 7/1949 | Pearson | |
| 3,172,892 A | 3/1965 | Le Suer et al. | |
| 3,202,678 A | 8/1965 | Stuart et al. | |
| 3,216,936 A | 11/1965 | Le Suer | |
| 3,219,666 A | 11/1965 | Norman et al. | |
| 3,254,025 A | 5/1966 | Le Suer | |
| 3,272,746 A | 9/1966 | Le Suer et al. | |
| 3,361,673 A | 1/1968 | Stuart et al. | |
| 3,676,089 A | 7/1972 | Morris et al. | |
| 4,038,043 A | 7/1977 | Garth | |
| 4,152,499 A | 5/1979 | Boerzel et al. | |
| 4,171,959 A | 10/1979 | Vartanian | |
| 4,231,759 A | 11/1980 | Udelhofen et al. | |
| 4,234,435 A | 11/1980 | Meinhardt et al. | |
| 4,248,719 A | 2/1981 | Chafetz | |
| 4,605,808 A | 8/1986 | Samson | |
| 4,613,341 A | 9/1986 | Zaweski et al. | |
| 4,729,769 A | 3/1988 | Schlicht et al. | |
| 4,847,714 A | 7/1989 | Vogel | |
| 4,877,416 A | 10/1989 | Cambell | |
| 5,254,138 A | 10/1993 | Kurek | |
| 5,358,873 A * | 10/1994 | Nowak | G01N 33/2882 436/60 |
| 5,393,309 A | 2/1995 | Cherpeck | |
| 5,498,808 A | 3/1996 | Smith | |
| 5,514,190 A | 5/1996 | Cunningham et al. | |
| 5,518,511 A | 5/1996 | Russel et al. | |
| 5,575,823 A | 11/1996 | Wallace et al. | |
| 5,620,486 A | 4/1997 | Cherpeck | |
| 5,634,951 A | 6/1997 | Colucci et al. | |
| 5,697,988 A | 12/1997 | Malfer et al. | |
| 5,725,612 A | 3/1998 | Malfer et al. | |
| 5,786,468 A | 7/1998 | Au et al. | |
| 5,814,111 A | 9/1998 | Graham et al. | |
| 5,873,917 A | 2/1999 | Daly | |
| 6,048,373 A | 4/2000 | Malfer et al. | |
| 6,166,238 A | 12/2000 | Filipowski et al. | |
| 6,458,172 B1 | 10/2002 | Macduff et al. | |
| 6,475,250 B2 | 11/2002 | Krull et al. | |
| 6,514,917 B1 * | 2/2003 | Smith | C09B 29/0809 44/328 |

(Continued)

FOREIGN PATENT DOCUMENTS

| | | |
|---|---|---|
| CA | 2089833 A1 | 8/1993 |
| CN | 1256302 A | 6/2000 |

(Continued)

OTHER PUBLICATIONS

Klonis, N. et al. "Spectral Properties of the Prototropic Forms of Fluorescein in Aqueous Solution," Journal of Fluorescence, vol. 6, No. 3, 1996, 147-157. (Year: 1996).*

Hakami, A.A.H. et al. "Extraction Procedures and Analytical Methods for the Determination of Methylene Blue, Rhodamine B and Crystal Violet—An Overview," Current Analytical Chemistry, vol. 17, Issue 5, 2021; pp. 1-21. (Year: 2021).*

Stephenson, C. J. et al. "A fluorescent diastereoselective molecular sensor for 1,2-aminoalcohols based on the rhodamine B lactone-zwitterion equilibrium," Org. Biomol. Chem., 2010, 8, 1027-1032 (Year: 2010).*

(Continued)

*Primary Examiner* — Jennifer Wecker
*Assistant Examiner* — Michelle Adams
(74) *Attorney, Agent, or Firm* — Honigman LLP

(57) ABSTRACT

The present disclosure provides methods for identifying a hydrocarbon fuel, such as the presence and/or amounts of marker compounds having a fluorescence intensity and, through correlation, the presence and/or amounts of additive package(s) within the hydrocarbon fuel. The methods include obtaining a sample of a hydrocarbon fuel including a marker compound having fluorescence, combining the hydrocarbon fuel with water, and subjecting a water phase thereof to light for observing fluorescence.

21 Claims, 3 Drawing Sheets

(56) References Cited

U.S. PATENT DOCUMENTS

| | | |
|---|---|---|
| 6,548,458 B2 | 4/2003 | Loper |
| 6,695,890 B1 | 2/2004 | Hazel et al. |
| 6,730,773 B2 | 5/2004 | Heinen |
| 6,800,103 B2 | 10/2004 | Malfer et al. |
| 6,867,171 B2 | 3/2005 | Harrison et al. |
| 6,991,914 B2 | 1/2006 | Park et al. |
| 7,402,185 B2 | 7/2008 | Aradi et al. |
| 7,435,272 B2 | 10/2008 | Aradi et al. |
| 7,704,289 B2 | 4/2010 | Arters et al. |
| 7,766,982 B2 | 8/2010 | Colucci et al. |
| 8,097,570 B2 | 1/2012 | Boutout et al. |
| 8,153,570 B2 | 4/2012 | Barton |
| 8,231,695 B2 | 7/2012 | Cunningham et al. |
| 8,425,627 B2 | 4/2013 | Dietz et al. |
| 8,449,630 B2 | 5/2013 | Lange et al. |
| 8,486,879 B2 | 7/2013 | Brewer et al. |
| 8,496,716 B2 | 7/2013 | Lange et al. |
| 8,529,643 B2 | 9/2013 | Galante-Fox et al. |
| 8,557,003 B2 | 10/2013 | Malfer et al. |
| 8,765,650 B2 | 7/2014 | Delbridge |
| 8,778,034 B2 | 7/2014 | Cunningham |
| 8,894,726 B2 | 11/2014 | Fang et al. |
| 9,005,988 B2 | 4/2015 | Perfect et al. |
| 9,951,285 B2 | 4/2018 | Roeger-Goepfert |
| 10,273,425 B2 | 4/2019 | Tabibi et al. |
| 10,308,888 B1 | 6/2019 | Schwab |
| 2004/0060226 A1 | 4/2004 | Bongart et al. |
| 2005/0066572 A1 | 3/2005 | Colucci et al. |
| 2005/0215411 A1 | 9/2005 | Mackney et al. |
| 2006/0070293 A1 | 4/2006 | Lange et al. |
| 2006/0168876 A1 | 8/2006 | Colucci et al. |
| 2006/0196110 A1 | 9/2006 | Schwahn et al. |
| 2006/0196111 A1 | 9/2006 | Colucci et al. |
| 2007/0245621 A1 | 10/2007 | Malfer et al. |
| 2008/0086936 A1 | 4/2008 | Cunningham et al. |
| 2009/0049740 A1 | 2/2009 | Hurst |
| 2009/0235576 A1 | 9/2009 | Volkel et al. |
| 2010/0005706 A1 | 1/2010 | Burgazli et al. |
| 2010/0132253 A1 | 6/2010 | Kaufman et al. |
| 2011/0162263 A1 | 7/2011 | Vilardo et al. |
| 2012/0138004 A1 | 6/2012 | Stevenson |
| 2013/0031828 A1 | 2/2013 | Reid |
| 2013/0104826 A1 | 5/2013 | Burgess |
| 2013/0237466 A1 | 9/2013 | Lange et al. |
| 2013/0247450 A1 | 9/2013 | Wolf |
| 2013/0255139 A1 | 10/2013 | Dolmazon et al. |
| 2013/0312318 A1 | 11/2013 | Peretolchin et al. |
| 2013/0227878 A1 | 12/2013 | Wolf et al. |
| 2013/0324665 A1 | 12/2013 | Shaikh et al. |
| 2014/0004615 A1* | 1/2014 | Wilkinson ............. C10L 1/003 422/82.05 |
| 2014/0157656 A1 | 6/2014 | Reid |
| 2014/0174390 A1 | 6/2014 | Reid |
| 2015/0212007 A1* | 7/2015 | Hoots ................ G01N 33/2852 250/206 |
| 2015/0252278 A1 | 9/2015 | Bush |
| 2016/0130514 A1 | 5/2016 | Hansch |
| 2016/0152910 A1 | 6/2016 | Reid |
| 2016/0152912 A1 | 6/2016 | Mulqueen |
| 2016/0272912 A1 | 9/2016 | Voelkel et al. |
| 2016/0289584 A1 | 10/2016 | Russo et al. |
| 2017/0096610 A1 | 4/2017 | Bush |
| 2017/0096611 A1 | 4/2017 | Stevenson |
| 2017/0101594 A1 | 4/2017 | Stevenson |
| 2017/0107438 A1 | 4/2017 | Greenfield |
| 2017/0114296 A1 | 4/2017 | Arters |
| 2017/0114297 A1 | 4/2017 | Sampler |
| 2017/0121628 A1 | 5/2017 | Moreton |
| 2017/0166826 A1 | 6/2017 | Culley |
| 2017/0218291 A1 | 8/2017 | Reid |
| 2018/0066202 A1 | 3/2018 | Gahagan |
| 2018/0223203 A1 | 8/2018 | Cook |

FOREIGN PATENT DOCUMENTS

| | | | |
|---|---|---|---|
| EP | 0016312 A1 | 10/1980 | |
| EP | 0820499 A1 | 1/1998 | |
| EP | 1293553 A2 | 3/2003 | |
| EP | 1411105 | 4/2004 | |
| EP | 1918355 | 5/2008 | |
| EP | 2531580 B1 | 11/2017 | |
| GB | 361310 A * | 11/1931 | |
| GB | 2493377 A1 | 2/2013 | |
| WO | WO-9622343 A1 * | 7/1996 | ............. C10L 1/003 |
| WO | 2004050806 | 6/2004 | |
| WO | 2005023965 A1 | 3/2005 | |
| WO | 2017097686 | 6/2017 | |

OTHER PUBLICATIONS

Karpiuk, J. et al. "Photophysics of the Lactone Form of Rhodamine 101," J. Phys. Chem. 1994, 98, 3247-3256 (Year: 1994).*

Mchedlov-Petrossyan, N.O. et al. "Dissociation, tautomerism and electroreduction of xanthene and sulfonephthalein dyes in N, N-dimethylformamide and other solvents," J. Phys. Org. Chem. 2003; 16: 380-397 (Year: 2003).*

Kaewtong, C. et al. "A solvatochromic-based sensor for chromium(III) in real systems," New J. Chem., 2018, 42, 9930. (Year: 2018).*

Murugesan, Sankaran et al. "Carbon Quantum Dots Fluorescent Tracers for Production and Well Monitoring." Paper presented at the SPE Annual Technical Conference and Exhibition, Dubai, UAE, Sep. 2016. doi: https://doi.org/10.2118/181503-MS, abstract only.

Tosch W. C. "Technique for Incorporating Water-Soluble Tracers in Hydrocarbon Media" Analytical Chemistry, vol. 37, No. 7, Jun. 1, 1965, pp. 959-959.

PCT; App. No. PCT/US2021/072073; International Search Report and Written Opinion mailed Feb. 22, 2022.

* cited by examiner

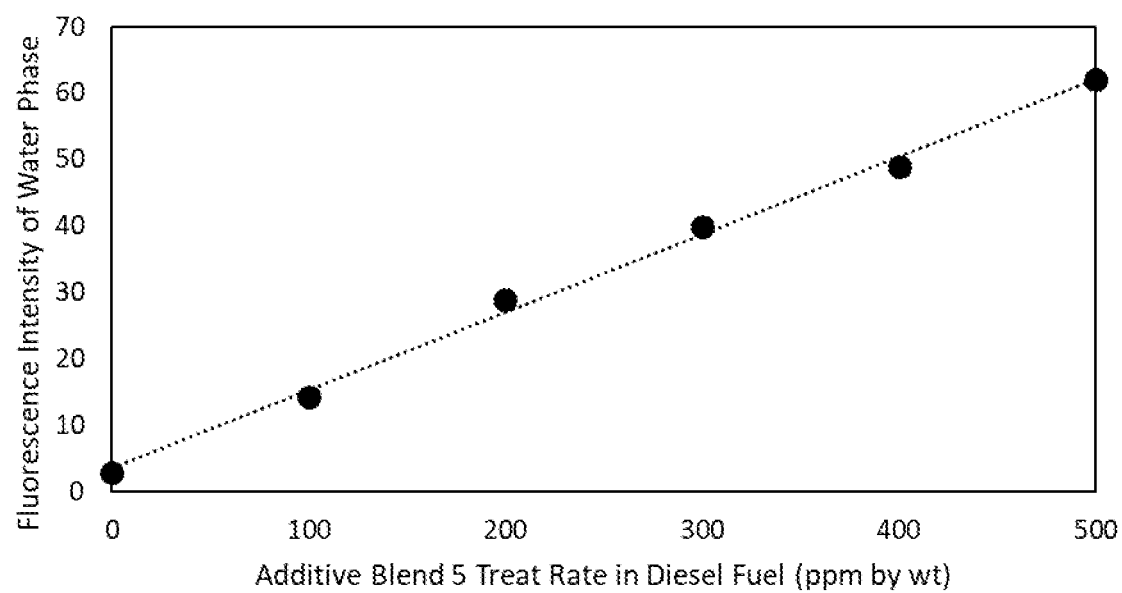

METHODS OF IDENTIFYING A HYDROCARBON FUEL

TECHNICAL FIELD

This disclosure is directed to methods of identifying a hydrocarbon fuel, and in particular, methods of identifying a hydrocarbon fuel using a marker compound having a fluorescence intensity.

BACKGROUND

Hydrocarbon fuel compositions for vehicles are continually being improved to enhance various performance properties of the fuels in order to accommodate their use in newer, more advanced engines. Each fuel brand often includes a select mix and amounts of additives that may be unique to the quality offered by that brand of fuel. Fuel companies often undertake substantial expenditures to ensure their branded fuel meets performance and quality standards. To this end, fuel companies often include within their branded fuel unique additive packages containing, for instance, select amounts of detergents, dispersants, friction modifiers, and many other compounds to achieve desired quality and performance. Consumers may rely upon the branded fuel and their advertised quality to assure that the product being purchased meets desired expectations.

Fuel companies, in some circumstances, often lose control of their product when it reaches the gas dealer or fueling station. In an effort to increase revenue or profits, end use providers could dilute a branded product with a lower quality one. Monitoring end use suppliers who alter or blend branded products with others can be challenging with gasoline or diesel hydrocarbon fuels because the unique blend of additives provided by the fuel companies are usually in very low levels and the blended products often qualitatively show the presence of each component found in the higher-quality branded fuels even when diluted. Conventional qualitative detection methods to determine the amounts and presence of very low levels of additive package components can be difficult, time consuming, and/or expensive.

Use of marker compounds have been proposed to permit detection of certain additives in hydrocarbon fuels, but prior compounds and methods have many shortcomings. Fluorescent markers have been proposed for such use in fuels, but both gasoline and diesel fuel has a native fluorescence that can overwhelm any usual fluorescence from such markers. Moreover, fluorescent markers are also often unstable in hydrocarbon fuels and/or either react with fuel additives or simply lose their fluorescence over time.

BRIEF DESCRIPTION OF THE FIGURES

FIG. 5 is a plot of additive treat rate versus fluorescence intensity of a marker compound in water phase.

SUMMARY

Figure 1:
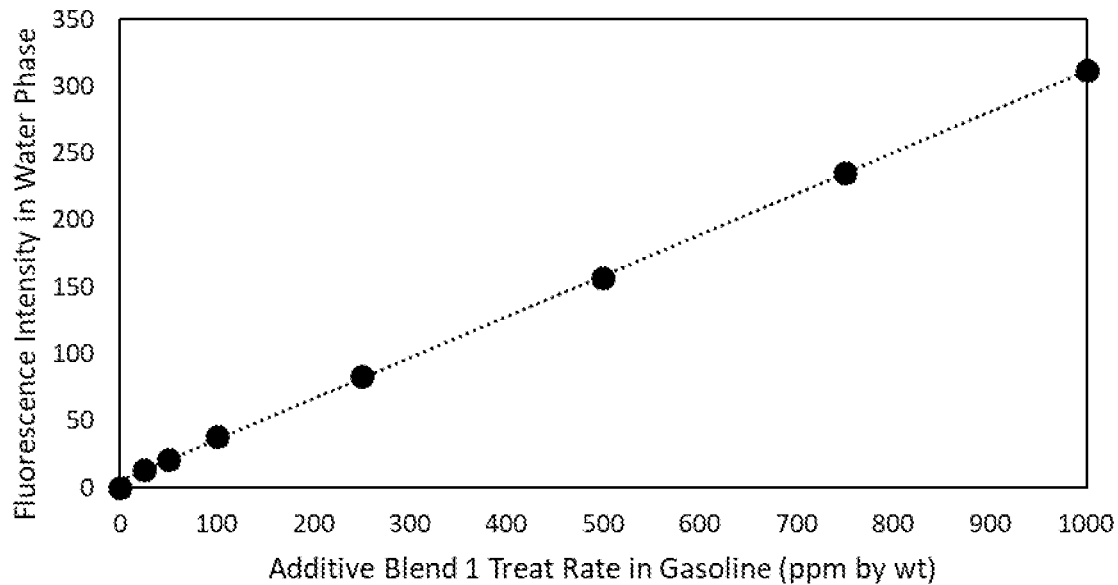
FIG. 1 is a plot of additive treat rate versus fluorescence intensity of a marker compound in water phase.

In one approach or embodiment, a method for identifying a hydrocarbon fuel is provided herein. The method includes obtaining a sample of a hydrocarbon fuel containing a measureable amount of a marker compound, the marker compound having a fluorescence intensity and at least partially soluble in water; combining the hydrocarbon fuel with water, and mixing the fuel and water mixture; after the mixing, allowing the fuel and water mixture to separate into a water phase and a fuel phase to at least partially extract the marker compound into the water phase; and subjecting the water phase to light having a wavelength of 250 nm to 800 nm and observing the fluorescence emitted from the marker compound in the water phase. In some approaches, the observing includes measuring a fluorescence intensity of the water phase and determining a concentration of the marker compound in the fuel based on the fluorescence intensity of the water phase with the at least partially extracted maker compound therein relative to a baseline fluorescence intensity of the water phase without the marker compound.

In other approaches or embodiments, the method of the previous paragraph may be combined with optional features and optional method steps in any combination thereof. These optional features, steps, or embodiments may include: wherein the fuel is selected from gasoline or diesel; and/or wherein the fuel is gasoline containing low alcohol (e.g., methanol, ethanol, or propanol); and/or wherein the gasoline contains at least about 2 volume percent ethanol; and/or wherein the fuel includes a fuel performance additive selected from the group consisting of detergents, antioxidants, carrier fluids, metal deactivators, corrosion inhibitors, biocides, antistatic additives, drag reducing agents, demulsifiers, emulsifiers, dehazers, anti-icing additives, antiknock additives, anti-valve-seat recession additives, lubricity additives, surfactants, combustion improvers, or combinations thereof and/or wherein the detergent is selected from the group consisting of Mannich reaction products formed by condensing a long-chain aliphatic hydrocarbon-substituted phenol or cresol with an aldehyde and an amine; long chain aliphatic hydrocarbons having an amine or a polyamine attached thereto; fuel-soluble nitrogen containing salts, amides, imides, succinimides, imidazolines, esters, and long chain aliphatic hydrocarbon-substituted dicarboxylic acids or their anhydrides or mixtures thereof; polyetheramines; and combinations thereof; and/or wherein a relationship between the fluorescence intensity and the concentration of marker compound in the fuel is linear within a concentration range of the marker compound of interest in the fuel; and/or wherein the fuel includes about 0.01 to about 100 parts per billion of the marker compound; and/or wherein a partition ratio of the marker compound between the water phase and fuel phase is at least about 0.1; and/or wherein the marker compound having a fluorescence intensity has a structure of Formula I:

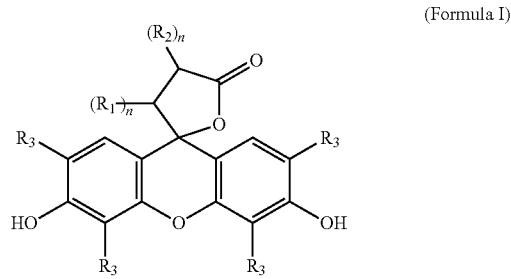

(Formula I)

and wherein $R_1$ and $R_2$ are independently hydrogen, a linear or branched alkyl group, or $R_1$ and $R_2$ may join to form a cyclic group or an aromatic group; n is an integer of 1 or 2; and each $R_3$ is hydrogen, a halogen atom, or a linear or branched C1 to C12 alkyl group; and/or wherein the marker compound having a fluorescence intensity has a structure of Formula II:

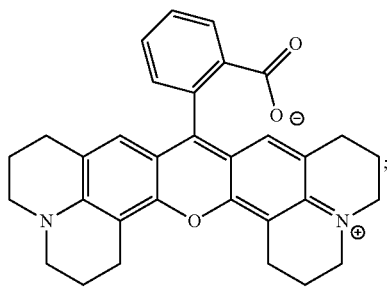

(Formula II)

and/or wherein the marker compound having a fluorescence intensity has a structure of Formula III:

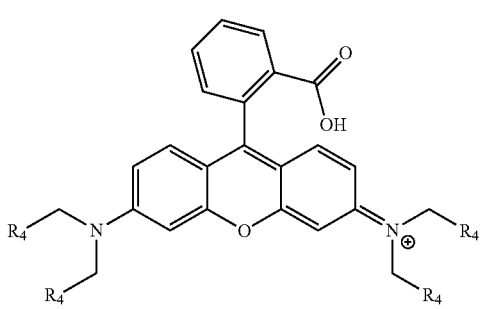

(Formula III)

and wherein each $R_4$ is independently a C1 to C10 alkyl group; and/or wherein the marker compound is first added to the fuel performance additive; and/or wherein the water includes a pH 4 to 10 buffer solution; and/or wherein the buffer solution includes dihydrogen potassium phosphate and dibasic sodium phosphate.

In other approaches or embodiments, a gasoline composition is also provided by the present disclosure. In aspects thereof, the gasoline composition includes a major amount of gasoline including at least about 2 volume percent ethanol; a gasoline performance additive including an additive selected from the group comprising detergents, antioxidants, carrier fluids, metal deactivators, corrosion inhibitors, biocides, antistatic additives, drag reducing agents, demulsifiers, emulsifiers, dehazers, anti-icing additives, antiknock additives, anti-valve-seat recession additives, lubricity additives, surfactants, combustion improvers, or combinations thereof; about 0.01 to about 100 parts per billion of a marker compound having a fluorescence intensity; and a partition ratio of the marker compound between water and gasoline of at least about 0.1.

In other embodiments or approaches, the gasoline composition of the previous paragraph may be combined with optional features and embodiments in any combination thereof. These optional features or embodiments may include: wherein the gasoline includes about 25 to about 1000 ptb (pounds per thousand barrels) of the fuel performance additive in the gasoline; and/or wherein the marker compound having a fluorescence intensity has a structure of Formula

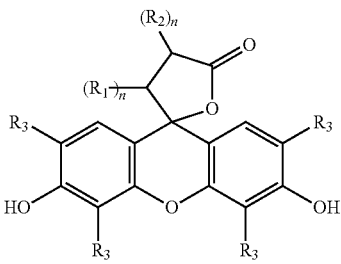

(Formula I)

wherein $R_1$ and $R_2$ are independently hydrogen, a linear or branched alkyl group, or $R_1$ and $R_2$ may join to form a cyclic group or an aromatic group; n is an integer of 1 or 2; and each $R_3$ is hydrogen, a halogen atom, or a linear or branched C1 to C12 alkyl group; and/or wherein the marker compound having a fluorescence intensity has a structure of Formula II:

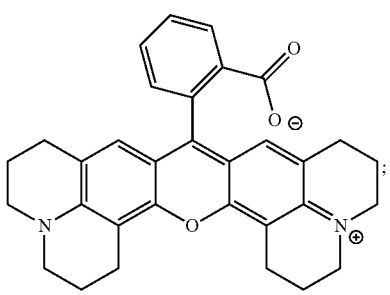

(Formula II)

and/or
wherein the marker compound having a fluorescence intensity has a structure of Formula III:

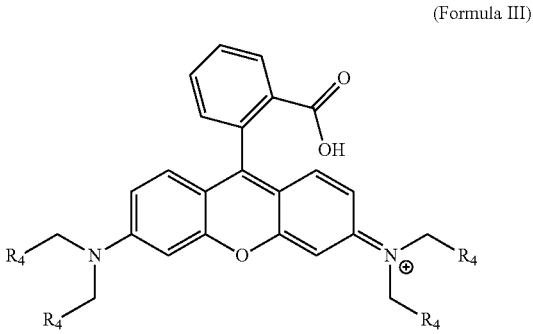

(Formula III)

and wherein each $R_4$ is independently a C1 to C10 alkyl group.

DETAILED DESCRIPTION

In one aspect, the present disclosure provides methods for identifying a hydrocarbon fuel, such as the presence and/or amounts of marker compounds having a fluorescence intensity and, through correlation, also identify the presence and/or amounts of additive package(s) within the hydrocarbon fuel. In one approach or embodiment, the methods herein include first obtaining a sample of a hydrocarbon fuel containing a measureable amount of a marker compound.

Preferably, the marker compound has a fluorescence intensity and is at least partially soluble in water. Next, the hydrocarbon fuel with the marker compound therein is combined with water to form a fuel and water mixture. The mixture is agitated to facilitate contact between the water and fuel. After the agitation, the fuel and water are allowed to separate into a water phase and a fuel phase to at least partially extract the marker compound into the water phase. Then, a fluorescence intensity of the water phase is measured and a concentration of the marker compound in the fuel (and thus, a concentration of the additive package in the fuel by correlation) is determined based on the fluorescence intensity of the water phase with the at least partially extracted maker compound therein. In some instances, the concentration may be corrected relative to a baseline fluorescence intensity of water or the water phase without the marker compound. The hydrocarbon fuel may include diesel, biodiesel, gasoline (also known as petrol), alcohol-based fuels, alcohol-blended fuels, or mixtures thereof. In particular, an alcohol-blended fuel may include a fuel, such as gasoline, blended with ethanol as described more below.

By ethanol herein is meant ethyl alcohol, the chemical compound $C_2H_5OH$. This can arise in or be provided in many qualities or grades, such a commercial fuel grade, as well as pure or reagent grade ethanol, and can be derived from any source such as but not limited to petroleum refinery streams, distillation cuts, and bio-derived (e.g. bioethanol such as from corn).

In some approaches of the method, the fuel is gasoline or diesel. In other approaches of the method, the fuel is gasoline and, preferably, gasoline with an amount of ethanol therein. In embodiments, the gasoline may contain at least about 2 volume percent ethanol (in other approaches, at least about 5 volume percent ethanol, at least about 10 volume percent ethanol, at least about 15 volume percent ethanol, at least about 20 volume percent ethanol, or at least about 25 volume percent ethanol and, in some approaches, less than about 50 volume percent ethanol, less than about 40 volume percent alcohol, less than about 30 volume percent ethanol, less than about 25 volume percent ethanol, or less than about 20 volume percent ethanol).

In yet other approaches of any embodiment of the methods herein, the fuel includes one or more fuel performance additives selected from the group consisting of detergents, antioxidants, carrier fluids, metal deactivators, corrosion inhibitors, biocides, antistatic additives, drag reducing agents, demulsifiers, emulsifiers, dehazers, anti-icing additives, antiknock additives, anti-valve-seat recession additives, lubricity additives, surfactants, combustion improvers, or combinations thereof.

In approaches of embodiments of the methods herein, the marker compound is at least partially soluble in water and, in some approaches, stable within the fuel and additive composition wherein the marker compound does not react with the hydrocarbon fuel and/or additives within the hydrocarbon fuel. Solubility between phases may be determined through a partition ratio. The partition ratio is defined herein as the equilibrium concentration of the marker compound in the water phase divided by the equilibrium concentration of the marker compound in the fuel phase. For instance, a partition ratio of the marker compound between the water and the fuel phases herein may be at least about 0.1, at least about 0.2, at least about 0.3 at least about 0.4, at least about 0.5, at least about 1, at least about 2, at least about 5, at least about 8, at least about 10, at least about 15, or even at least about 20 and less than 30, less than 25, less than 20, less than 15, or even less than 10. Partition ratios greater than 1 mean the marker compound is more soluble in water than fuel and partition ratios less than one mean the marker compound is partially soluble in water.

In some approaches of the methods, the selected marker compound demonstrates a linear relationship or correlation between the fluorescence intensity and the concentration of marker compound in the fuel within a concentration range of the marker compound of interest in the fuel. To this end, approaches of the methods herein include the fuel having about 0.01 to about 100 parts per billion (ppb) of the marker compound, in other approaches, about 0.5 to 70 ppb, about 1 to about 50 ppb, about 1 to about 30 ppb, about 1 to about 20 ppb, about 1 to about 15 ppb, or about 1 to about 10 ppb of the marker compound (or other ranges therewithin). Preferably, the relationship between the fluorescence intensity of the marker compound and concentration of the marker compound is linear within such amounts of the marker compounds in the fuels herein.

In one approach, the marker compound having a fluorescence intensity suitable for the methods herein has a structure of Formula I:

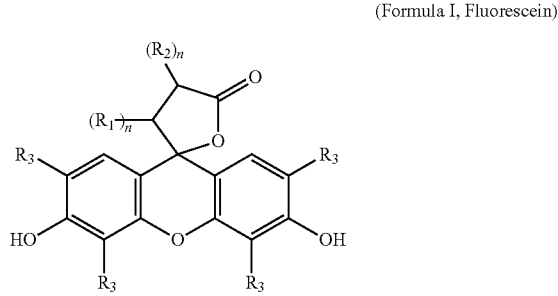

(Formula I, Fluorescein)

wherein $R_1$ and $R_2$ are independently hydrogen, a linear or branched alkyl group, or $R_1$ and $R_2$ may join to form a cyclic group or an aromatic group; n is an integer of 1 or 2; and each $R_3$ is hydrogen, a halogen atom, or a linear or branched C1 to C12 alkyl group In other approaches, the marker compound having a fluorescence intensity suitable for the methods herein has a structure of Formula II:

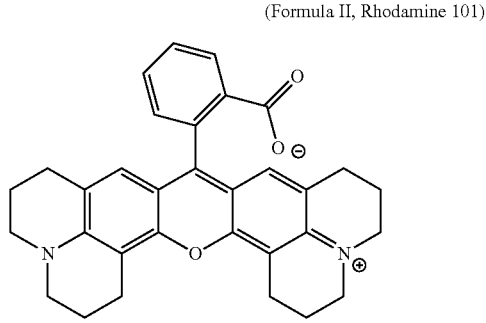 [SMILES: O=C([O-])c1ccccc1C1=c2cc3c4c(c2Oc2c1cc1c5c2CCCN5CCC1)CCC[N+]=4CCC3]

(Formula II, Rhodamine 101)

In yet further approaches, the marker compound having a fluorescence intensity suitable for the methods herein has a structure of Formula III:

(Formula III, Rhodamine B)

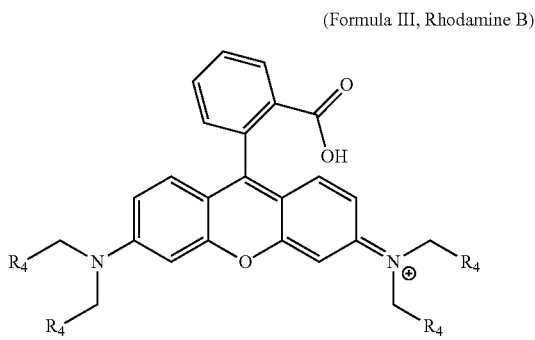

wherein each $R_4$ is independently a C1 to C10 alkyl group. Such marker compounds of Formula I, II, and/or III have surprisingly demonstrated the desired water solubility, partition ratio, stability in typical additive packages, and stability in hydrocarbon fuels having an additive package therein. In some approaches, the marker compounds herein are free of non-cyclic ester groups and, in some approaches, free of non-cyclic ester groups means that hydroxyl groups on marker compound ring structures are not esterified as further shown by the marker compound structures herein. Surprisingly, the marker compounds without non-cyclic ester groups still function within the methods herein.

In some approaches of the method, the select marker compound is first added to a fuel performance additive, such as a gasoline or diesel performance additive. These additives may include select amounts of detergents, antioxidants, carrier fluids, metal deactivators, corrosion inhibitors, biocides, antistatic additives, drag reducing agents, demulsifiers, emulsifiers, dehazers, anti-icing additives, antiknock additives, anti-valve-seat recession additives, lubricity additives, surfactants, combustion improvers, or combinations thereof. The fuel performance additive may include about 1 to about 100 ppm of the marker compound, in other approaches, about 0.1 to about 75 ppm of the marker compound, or about 1 to about 50 ppm of the marker compound.

The fuels herein may include about 1 to about 5000 ppm of the fuel performance additive package with the marker compound therein. In other approaches, the fuel may include up to about 4000 ppm, up to about 3000 ppm, up to about 2000 ppm, up to about 1000 ppm, up to about 900 ppm, up to about 800 ppm, up to about 600 ppm, up to about 550 ppm, up to about 400 ppm, up to about 200 ppm, up to about 150 ppm, up to about 100, ppm, up to about 60 ppm, up to about 50 ppm, or up to about 30 ppm of the fuel performance additive package. In embodiments, the fuel may also include at least about 20 ppm of the fuel performance additive package, or at least about 40 ppm, at least about 70 ppm, at least about 90 ppm, at least about 150 ppm, at least about 200 ppm, at least about 300 ppm, at least about 400 ppm, at least about 450 ppm, at least about 500 ppm, at least about 900 ppm, at least about 1500 ppm, or at least about 2000 ppm. The fuel performance additive package including the marker compound may be blended with the desired fuel source.

When the hydrocarbon fuel is desired to be analyzed or identified, a sample of the fuel is taken. The amount of fuel in the test sample is not particularly limited, but is usually less than about 100 ml, such as about 2 to about 25 ml of fuel, or about 2 to about 10 ml of the fuel to be analyzed. The fuel is then combined with water by either adding the fuel to the water or, alternatively, adding water to the fuel to form a fuel and water mixture. The amount of water used is about 1 to about 5 ml, or preferably, about 1 to about 3 ml of water. To improve the fluorescence signal, water may be added in a lower amount than the fuel, which may increase the concentration of the marker compound in the water phase. In some approaches, the ratio of fuel to water is about 5:1 to about 1:1. For gasoline, the ratio may be about 1:1 to about 3.5:1 (or 1:1 to about 3:1 or about 3:1) and for diesel, the ratio may be 1:1 to about 3:1 (or 1:1 to about 2.6:1 or about 2.6:1). For gasoline including ethanol, some of the ethanol added to or included with the gasoline may enter the water phase, thus increasing the total volume of that phase. Generally only water separates from diesel and, thus, more water is generally needed for evaluation of the marker compound in diesel fuels. The water may be a distilled or deionized water or, optionally, a buffered water solution, such as pH 4 to 10 buffer solutions (in other approaches, a pH 6 to 8 buffer solution). In embodiments, the buffer solution may be a 0.05 molar, pH 7 dihydrogen potassium phosphate and sodium phosphate dibasic buffer solution.

The fuel and water mixture is gently mixed, shaken, or agitated. The mixture is then allowed to separate into a water and a fuel phase. Typically, the water phase is analyzed within an appropriate container or vessel, such as a 10 mm NMR tube for instance (but any suitable glass or clear walled tube or container may be used). Suitable gentle mixing, shaking, or agitation may be accomplished by gently shaking for about 30 seconds to about 2 minutes, or simply by inverting the NMR tube (or other container) 8 to 30 times, preferably 15 to 25 times, and most preferably, 20 times; however, other comparable gentle mixing procedures may be used.

After mixing, the mixture is allowed sit for a period of time so that the mixture may again separate into fuel and water phases. In some approaches, the mixture is allowed to sit and separate for about 1 to about 15 minutes, about 2 to about 10 minutes, or about 3 to about 5 minutes. During this separation phase time, the select marker compounds herein are at least partially extracted or at least partially partitioned into the water phase. The color bodies typically found in commercial gasoline or diesel fuels do not partition into the water phase, but remain in the fuel phase. Thus, any additives or other compounds in gasoline or diesel would not interfere with the water phase fluorescence. As explained above, a partition ratio of the marker compound between the water and the fuel phases herein may be at least about 0.1, at least about 0.2, at least about 0.3 at least about 0.4, at least about 0.5, at least about 1, at least about 2, at least about 5, at least about 8, at least about 10, at least about 15, or even at least about 20 and less than 30, less than 25, less than 20, less than 15, or even less than 10. Partition ratios greater than 1 mean the marker compound is more soluble in water than fuel and partition ratios less than one mean the marker compound is partially soluble in water.

After the mixture is allowed to separate, a fluorescence intensity of the water phase (with the extracted marker compound therein) is then measured. Fluorescence measurements may be conducted using a Perkin Elmer 204-a Fluorescence Spectrophotometer equipped with a tungsten-halogen light source. However, other suitable spectrophotometers may also be used. In approaches of the methods herein, the spectrophotometer was operated with slit widths set to about 10 mm for both excitation and emission wavelengths. If needed, an initial fluorescence intensity of the water before mixing and separation may be performed to determine any background noise or background fluorescence of the water used in the testing. Excitation wavelengths for the testing may range from about 250 nm to about 800 nm and may vary depending on the selected marker compound. Emission wavelength for the testing may range from about 300 nm to about 900 nm and may also vary depending on the selected marker compound. For instance, marker compound of Formula 1 may have an excitation wavelength of 450 to 480 nm and preferably 470 nm and an emission wavelength of about 500 to about 550 nm and preferably 515 nm. The marker compound of Formula II may have an excitation wavelength of 520 to 560 nm and preferably 540 nm and an emission wavelength of about 580 to about 660 nm and preferably 590 nm. The marker compound of Formula III may have an excitation wavelength of 530 to 550 nm and preferably 540 nm and an emission wavelength of about 580 to about 600 nm and preferably 590 nm.

The spectrophotometer reports the fluorescence intensity, which those of ordinary skill appreciate is an arbitrary unit of measure reported from the instrument. From the measured fluorescence intensity, the concentration of marker compound (and thus the concentration of fuel performance additive) in the fuel can be determined because the concentration of the marker compound in the fuel (and thus, the amount of fuel performance additive in the fuel) is directly proportional to the fluorescence intensity (and preferably a linear relationship) within the concentration range of interest within the fuel. The identity of the hydrocarbon fuel can then be confirmed by ascertaining if the concentration of the fuel performance additive is within specification.

Hydrocarbon Fuels: The hydrocarbon fuels of the present application may be applicable to the operation of diesel, jet, or gasoline engines. In one approach, the marker compounds herein are well suited for diesel or gasoline and, particularly, gasoline, and even more particularly, gasoline having an amount of ethanol therein. In one embodiment, the fuel is gasoline and, in another embodiment, gasoline having ethanol therein. In other another embodiment, the fuel is a diesel. The fuels may include any and all middle distillate fuels, diesel fuels, biorenewable fuels, biodiesel fuel, fatty acid alkyl ester, gas-to-liquid (GTL) fuels, gasoline, jet fuel, alcohols, ethers, kerosene, low sulfur fuels, synthetic fuels, such as Fischer-Tropsch fuels, liquid petroleum gas, bunker oils, coal to liquid (CTL) fuels, biomass to liquid (BTL) fuels, high asphaltene fuels, fuels derived from coal (natural, cleaned, and petcoke), genetically engineered biofuels and crops and extracts therefrom, and natural gas. "Biorenewable fuels" as used herein is understood to mean any fuel which is derived from resources other than petroleum. Such resources include, but are not limited to, corn, maize, soybeans and other crops; grasses, such as switchgrass, miscanthus, and hybrid grasses; algae, seaweed, vegetable oils; natural fats; and mixtures thereof. In an aspect, the biorenewable fuel can comprise monohydroxy alcohols, such as those comprising from 1 to about 5 carbon atoms. Non-limiting examples of suitable monohydroxy alcohols include methanol, ethanol, propanol, n-butanol, isobutanol, t-butyl alcohol, amyl alcohol, isoamyl alcohol, and mixtures thereof. Preferred fuels include gasoline fuels.

The methods herein are particularly suited for use on alcohol-blended fuels, such as a fuel, gasoline, blended with ethanol. A common ethanol-blended fuel is E10, which is a blend of 10 volume % ethanol and 90 volume % gasoline. The fuels may include amounts of ethanol as described above. Other ethanol based fuels may include, for example 85 volume % ethanol (E85), 50 volume % ethanol (E50), or 100 volume % ethanol (E100). E10, gasoline, and diesel are seasonally adjusted to ensure proper starting and performance in different geographic locations.

The fuels herein are suitable for use in various internal combustion systems or engines. The systems or engines may include both stationary engines (e.g., engines used in electrical power generation installations, in pumping stations, etc.) and ambulatory engines (e.g., engines used as prime movers in automobiles, trucks, road-grading equipment, military vehicles, etc.). By combustion system or engine herein is meant, internal combustion engines, for example and not by limitation, Atkinson cycle engines, rotary engines, spray guided, wall guided, and the combined wall/spray guided direct injection gasoline ("DIG" or "GDI") engines, turbocharged DIG engines, supercharged DIG engines, homogeneous combustion DIG engines, homogeneous/stratified DIG engines, DIG engines outfitted with piezoinjectors with capability of multiple fuel pulses per injection, DIG engines with EGR, DIG engines with a lean-NOx trap, DIG engines with a lean-NOx catalyst, DIG engines with SN-CR NOx control, DIG engines with exhaust diesel fuel after-injection (post combustion) for NOx control, DIG engines outfitted for flex fuel operation (for example, gasoline, ethanol, methanol, biofuels, synthetic fuels, natural gas, liquefied petroleum gas (LPG), and mixtures thereof) Also included are conventional and advanced port-fueled internal combustion engines, with and without advanced exhaust after-treatment systems capability, with and without turbochargers, with and without superchargers, with and without combined supercharger/turbocharger, with and without on-board capability to deliver additive for combustion and emissions improvements, and with and without variable valve timing. Further included are gasoline fueled homogeneous charge compression ignition (HCCI) engines, diesel HCCI engines, two-stroke engines, diesel fuel engines, gasoline fuel engines, stationary generators, gasoline and diesel HCCI, supercharged, turbocharged, gasoline and diesel direct injection engines, engines capably of variable valve timing, leanburn engines, engines capable of inactivating cylinders or any other internal combustion engine. Still further examples of combustion systems include any of the above-listed systems combined in a hybrid vehicle with an electric motor.

Fuel Performance Additives: The base hydrocarbon fuel may contain an additive package or concentrate including one or more optional fuel additives. For example, the additive packages herein and/or the fuels may contain conventional quantities of detergents, cetane improvers, octane improvers, corrosion inhibitors, cold flow improvers (CFPP additive), pour point depressants, solvents, demulsifiers, lubricity additives, friction modifiers, amine stabilizers, combustion improvers, dispersants, antioxidants, heat stabilizers, conductivity improvers, metal deactivators, marker dyes, organic nitrate ignition accelerators, cycloaromatic manganese tricarbonyl compounds, carrier fluids, antifoam agents, and the like appropriate for the type of fuel. In some aspects, the compositions described herein may contain about 10 weight percent or less, or in other aspects, about 5 weight percent or less, based on the total weight of the additive package or concentrate, of one or more of the above additives. Similarly, the fuels may contain suitable amounts of conventional fuel blending components such as methanol, ethanol, butanol, dialkyl ethers, 2-ethylhexanol, fatty acid methyl esters (FAME, biodiesel) and the like. If used, the fuel preferably includes at least about 1 volume percent of such fuel blending components, and in other embodiments, about 2 to about 20 volume percent, or about 2 to about 15 volume percent, or about 2 to about 10 volume percent. In some approaches, the fuel blending component is ethanol.

In some aspects of the disclosed embodiments, organic nitrate ignition accelerators that include aliphatic or cycloaliphatic nitrates in which the aliphatic or cycloaliphatic group is saturated, and that contain up to about 12 carbons may be used. Examples of organic nitrate ignition accelerators that may be used are methyl nitrate, ethyl nitrate, propyl nitrate, isopropyl nitrate, allyl nitrate, butyl nitrate, isobutyl nitrate, sec-butyl nitrate, tert-butyl nitrate, amyl nitrate, isoamyl nitrate, 2-amyl nitrate, 3-amyl nitrate, hexyl nitrate, heptyl nitrate, 2-heptyl nitrate, octyl nitrate, isooctyl nitrate, 2-ethylhexyl nitrate, nonyl nitrate, decyl nitrate, undecyl nitrate, dodecyl nitrate, cyclopentyl nitrate, cyclohexyl nitrate, methylcyclohexyl nitrate, cyclododecyl nitrate, 2-ethoxyethyl nitrate, 2-(2-ethoxyethoxy)ethyl nitrate, tetrahydrofuranyl nitrate, and the like. Mixtures of such materials may also be used.

Examples of suitable optional metal deactivators useful in the compositions of the present application are disclosed in U.S. Pat. No. 4,482,357, the disclosure of which is herein incorporated by reference in its entirety. Such metal deactivators include, for example, salicylidene-o-aminophenol, disalicylidene ethylenediamine, di salicylidene propylenediamine, and N,N'-disalicylidene-1,2-diaminopropane.

Suitable optional cycloaromatic manganese tricarbonyl compounds which may be employed in the compositions of the present application include, for example, cyclopentadienyl manganese tricarbonyl, methylcyclopentadienyl manganese tricarbonyl, indenyl manganese tricarbonyl, and ethylcyclopentadienyl manganese tricarbonyl. Yet other examples of suitable cycloaromatic manganese tricarbonyl compounds are disclosed in U.S. Pat. Nos. 5,575,823 and 3,015,668, both of which are incorporated by reference in their entirety.

Suitable detergents include but are not limited to succinimides, Mannich base detergents, quaternary ammonium compounds, bis-aminotriazole detergents as generally described in U.S. Pat. No. 8,529,643; US 2012/0010112; and/or U.S. Pat. No. 10,308,888 (which are all incorporated herein by reference), or a reaction product of a hydrocarbyl substituted dicarboxylic acid, or anhydride and an aminoguanidine, wherein the reaction product has less than one equivalent of amino triazole group per molecule as generally described in U.S. Pat. Nos. 8,758,456 and/or 8,852,297, which are both incorporated herein by reference.

In some approaches, the detergent is selected from the group consisting of Mannich reaction products formed by condensing a long-chain aliphatic hydrocarbon-substituted phenol or cresol with an aldehyde and an amine; long chain aliphatic hydrocarbons having an amine or a polyamine attached thereto; fuel-soluble nitrogen containing salts, amides, imides, succinimides, imidazolines, esters, and long chain aliphatic hydrocarbon-substituted dicarboxylic acids or their anhydrides or mixtures thereof; polyetheramines; and combinations thereof.

Suitable carrier fluids may be selected from any suitable carrier fluid that is compatible with the gasoline and is capable of dissolving or dispersing the components of the additive concentrate. Typically, the carrier fluid is a hydrocarbyl polyether or a hydrocarbon fluid, for example a petroleum or synthetic lubricating oil basestock including mineral oil, synthetic oils such as polyesters or polyethers or other polyols, or hydrocracked or hydroisomerised basestock. Alternatively, the carrier fluid may be a distillate boiling in the gasoline range. The amount of carrier fluid contained in the additive concentrate may range from 10 to 80 wt. %, or from 20 to 75 wt. %, or from 30 to 60 wt. % based on a total weight of the additive concentrate. Such additive concentrates containing the inventive components, detergent and carrier fluid were found to remain as clear fluids even at temperatures as low as −20° C.

The additives of the present application, including the marker compounds as described above, and any optional additives used in formulating the fuels of this disclosure may be blended into the base fuel individually or in various sub-combinations. In some embodiments, the marker compounds of the present application may be blended into the fuel concurrently using an additive concentrate, as this takes advantage of the mutual compatibility and convenience afforded by the combination of ingredients when in the form of an additive concentrate. In yet other approaches, the marker compound is first blended with the fuel performance additive or concentrate, which is then blended into the fuel. Also, use of a concentrate may reduce blending time and lessen the possibility of blending errors.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having a predominantly hydrocarbon character. Each hydrocarbyl group is independently selected from hydrocarbon substituents, and substituted hydrocarbon substituents containing one or more of halo groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents are present for every ten carbon atoms in the hydrocarbyl group.

As used herein, the term "percent by weight" or "wt %", unless expressly stated otherwise, means the percentage the recited component represents to the weight of the entire composition.

The term "alkyl" if used herein, unless specified otherwise, refers to straight, branched, cyclic, and/or substituted saturated chain moieties of from about 1 to about 200 carbon atoms.

The term "alkenyl" if used herein, unless specified otherwise, refers to straight, branched, cyclic, and/or substituted unsaturated chain moieties of from about 3 to about 30 carbon atoms.

The term "aryl" if used herein, unless specified otherwise, refers to single and multi-ring aromatic compounds that may include alkyl, alkenyl, alkylaryl, amino, hydroxyl, alkoxy, halo substituents, and/or heteroatoms including, but not limited to, nitrogen, and oxygen.

As used herein, the "molecular weight" or "MW" if used herein, unless specified otherwise, is determined by gel permeation chromatography (GPC) using commercially available polystyrene standards (with a Mn of 180 to about 18,000 as the calibration reference).

EXAMPLES

The following examples are illustrative of exemplary embodiments of the disclosure. In these examples, as well as elsewhere in this application, all ratios, parts, and percentages are by weight unless otherwise indicated. It is intended that these examples are being presented for the purpose of illustration only and are not intended to limit the scope of the invention disclosed herein.

Example 1

For this example, the fluorescence of various unmodified marker compounds were evaluated. The general protocol involved obtaining a measured amount of fuel treated with an additive package with a fluorescent marker therein was first dispensed into a clear glass vial. Then, a measured amount of distilled water or buffered water solution as noted below was added to the vial. The vial with gently agitated (inverted 20 times) to mix the water and fuel. The samples were allowed to sit at room temperature (20 to 25° C.) for 5 minutes to allow the water and fuel phases to separate. Then, the fluorescence intensity of the marker in the water phase, at the appropriate excitation and emission wavelengths, was measured and plotted against the concentration of the additive blend. This plot can serve as a calibration curve.

For all analyses involving gasoline samples, 15 grams of gasoline and 5 grams of water were used. For all analyses involving diesel fuel samples, 18 grams of diesel fuel and 7 grams of water were used. About 7 ml of separated water is needed in the vial to allow the excitation beam of the instrument (a Perkin Elmer 204-A) used to measure fluorescence intensity to pass only through the water phase. As the gasoline evaluated included ethanol (described below), which migrates into the water phase increasing its volume, less water is generally needed for gasoline.

In this Example, marker compounds evaluated where Rhodamine B, Rhodamine 101 Rhodamine 6G, or Fluorescein and each marker compound was unmodified and, thus, devoid of non-cyclic ester groups or non-cyclic ester moieties. For all analyses involving Rhodamine B, Rhodamine 101 and Rhodamine 6G, unbuffered distilled water was used. For all analyses involving Fluorescein, a buffered water solution (pH=7) was used.

The gasoline used in the examples was obtained from a pipeline terminal in Richmond Virginia and contained 10 volume % ethanol. The diesel used in the examples was No. 2 ultra-low sulfur diesel fuel and was obtained from the same terminal.

Fluorescence measurements were made with a Perkin Elmer 204-A Fluorescence Spectrophotometer equipped with a tungsten-halogen light source. Slit widths were set to 10 mm for both the excitation and emission wavelengths. The sample vial was arranged in the instrument such that the excitation beam passed only through the water (lower) phase. The gasoline included an additive base composition of Table 1 and the diesel included an additive base composition of Table 2. Fluorescence intensity was as reported by the spectrophotometer.

TABLE 1

| Gasoline additive base composition (Blend 1): | |
| --- | --- |
| Component | Concentration (wt. %) |
| Detergent | 36.0 |
| Carrier Fluid | 15.0 |
| Demulsifier | 1.0 |
| Corrosion Inhibitor | 0.5 |
| Solvent | 47.5 |

The detergent in Blend 1 was a Mannich reaction product of a 1000 Mn polyisobutylene substituted cresol reacted with formaldehyde and an amine.

TABLE 2

| Diesel additive base composition (Blend 2): | |
| --- | --- |
| Component | Concentration (wt. %) |
| Detergent | 25.0 |
| Demulsifier | 1.5 |
| Antifoam Agent | 2.0 |
| Corrosion Inhibitor | 0.5 |
| Solvent | 71.0 |

The detergent in Blend 2 was a quaternary ammonium additive synthesized according to the procedure given for Preparation Example 1 in US 2012/0010112 A1.

Blend 1 or Blend 2 was combined with a base fuel (gasoline or diesel) according to the amounts in Table 3 and Table 4 below.

TABLE 3

Additive blends with markers

Concentration (wt. %)

| Sample | Blend 1 | Blend 2 | TOFA | Fluorescein | Rhodamine 101 | Rhodamine B | Rhodamine 6G |
| --- | --- | --- | --- | --- | --- | --- | --- |
| 1 | 99.999 | | | 0.001 | | | |
| 2 | 99.997 | | | | 0.003 | | |
| 3 | 99.997 | | | | | 0.003 | |
| 4 | | | 99.999 | 0.001 | | | |
| 5 | | 99.9993 | | | 0.0007 | | |
| 6 | 99.997 | | | | | | 0.003 |

When gasoline treated with fuel sample 6 was subjected to the analysis procedure, the water layer did not produce any measurable fluorescence above the baseline (untreated fuel) even though Rhodamine 6G fluoresces strongly in water. Thus, it appears that Rhodamine 6G is not stable in the fuel or fuel additive and reacts with some component in the additive base composition, with the resulting product being non-fluorescent. The fluorescence intensity of the water phase 5 to 10 minutes after agitation from the other marker compounds and samples is reported in Table 4. (Fluorescence intensity is corrected for any background fluorescence and stray light from the water as exemplified in the next Example)

TABLE 4

Fluorescence Intensity of water layer after extraction according to procedure:

| Sample | Fuel Type | Treat Rate of Additive Blend in Fuel (ppm by wt.) | Excitation Wavelength (nm) | Emission Wavelength (nm) | Fluorescence Intensity (Arbitrary Units) |
|---|---|---|---|---|---|
| Baseline | Gasoline | — | 470 | 515 | 0.7 |
| Baseline | Gasoline | — | 540 | 590 | 0.5 |
| 1 | Gasoline | 1000 | 470 | 515 | 311.7 |
| 1 | Gasoline | 750 | 470 | 515 | 235.0 |
| 1 | Gasoline | 500 | 470 | 515 | 156.7 |
| 1 | Gasoline | 250 | 470 | 515 | 83.0 |
| 1 | Gasoline | 100 | 470 | 515 | 38.5 |
| 1 | Gasoline | 50 | 470 | 515 | 21.0 |
| 1 | Gasoline | 25 | 470 | 515 | 13.7 |
| 2 | Gasoline | 1000 | 540 | 590 | 206.7 |
| 2 | Gasoline | 750 | 540 | 590 | 153.3 |
| 2 | Gasoline | 500 | 540 | 590 | 102.5 |
| 2 | Gasoline | 250 | 540 | 590 | 52.0 |
| 2 | Gasoline | 100 | 540 | 590 | 16.0 |
| 2 | Gasoline | 50 | 540 | 590 | 7.5 |
| 3 | Gasoline | 1000 | 540 | 590 | 281.7 |
| 3 | Gasoline | 750 | 540 | 590 | 243.3 |
| 3 | Gasoline | 500 | 540 | 590 | 160.0 |
| 3 | Gasoline | 250 | 540 | 590 | 77.0 |
| 3 | Gasoline | 100 | 540 | 590 | 35.0 |
| Baseline | Diesel Fuel | — | 470 | 515 | 6.5 |
| Baseline | Diesel Fuel | — | 540 | 590 | 2.9 |
| 4 | Diesel Fuel | 500 | 470 | 515 | 223.3 |
| 4 | Diesel Fuel | 250 | 470 | 515 | 111.7 |
| 4 | Diesel Fuel | 100 | 470 | 515 | 48.0 |
| 4 | Diesel Fuel | 75 | 470 | 515 | 41.0 |
| 4 | Diesel Fuel | 50 | 470 | 515 | 27.7 |
| 4 | Diesel Fuel | 25 | 470 | 515 | 14.0 |
| 5 | Diesel Fuel | 500 | 540 | 590 | 62.0 |
| 5 | Diesel Fuel | 400 | 540 | 590 | 49.0 |
| 5 | Diesel Fuel | 300 | 540 | 590 | 40.0 |
| 5 | Diesel Fuel | 200 | 540 | 590 | 29.0 |
| 5 | Diesel Fuel | 100 | 540 | 590 | 14.3 |

Figure 2:
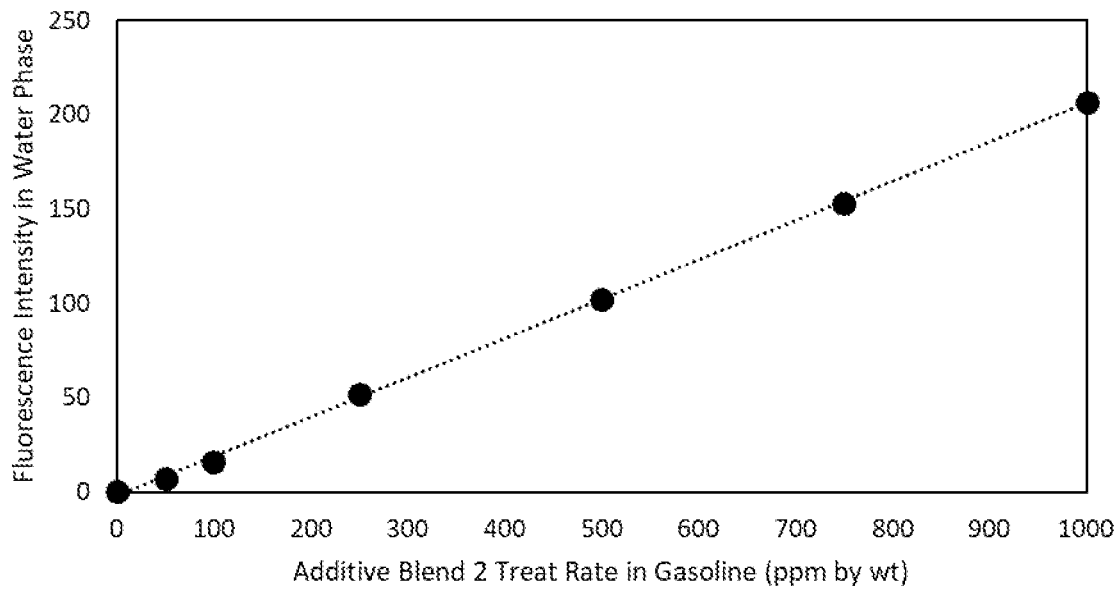
FIG. 2 is a plot of additive treat rate versus fluorescence intensity of a marker compound in water phase.
Figure 3:
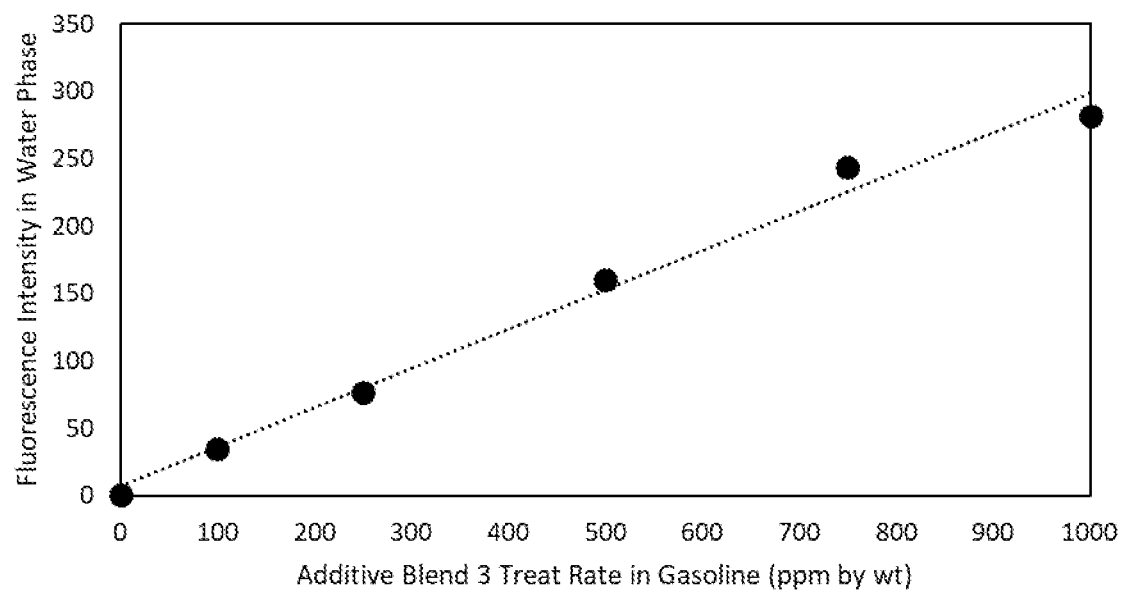
FIG. 3 is a plot of additive treat rate versus fluorescence intensity of a marker compound in water phase.
Figure 4:
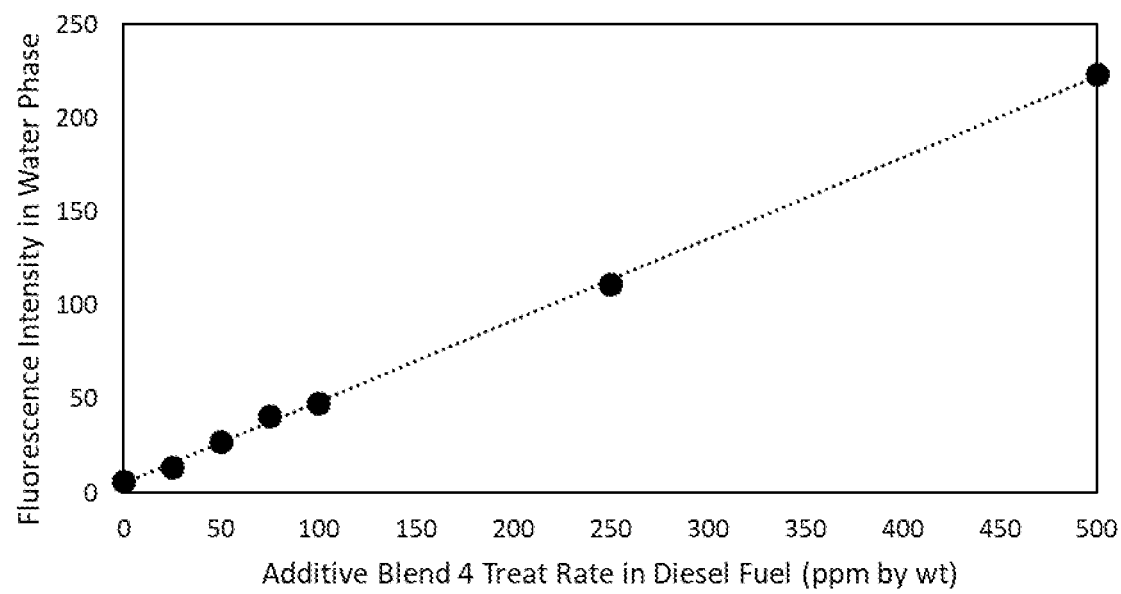
FIG. 4 is a plot of additive treat rate versus fluorescence intensity of a marker compound in water phase.

The data from the table 4 is plotted in FIGS. 1 to 5 showing the linear correlations between the fluorescence intensity of the water layer relative to the treat rate of the additive composition in the fuel.

Example 2

In this Example, the separation/partition of the marker compound between water and fuel phases was measured. The procedure for this Example included: measure fluorescence of 10 grams of water phase with and without marker compound present to determine background fluorescence. Then, 10 grams of hydrocarbon including 10 ppb of marker compound was added to the water and gently agitated for 1 minute. After mixing, the sample was allowed to completely separate into two phases. Thereafter, the fluorescence of the water phase was re-measured. Since the marker concentration is directly proportional to fluorescence intensity (at 10 ppb and within a range of interest), the Partition Ratio can be calculated from the initial and final tracer fluorescence intensities (corrected for any background fluorescence) from the water phase.

For this Example, Rhodamine B, Rhodamine 101, and Fluorescein marker compounds were used. For Rhodamine 101 and Rhodamine B measurements, excitation wavelength was 540 nm and emission wavelength was 590 nm. For Fluorescein measurements, excitation wavelength was 470 nm and emission wavelength was 515 nm. The measured fluorescence and partition ratio is shown in Table 5 below.

TABLE 5

| Marker | Hydrocarbon | Initial Fluorescence Intensity in Water Phase (arb units) | Fluorescence Intensity in Water Phase After Partition (arb units) | Partition Ratio (Kd) |
|---|---|---|---|---|
| None | Heptane | 0 | 1 | — |
| None | Gasoline | 0 | 0.5 | — |
| Rhodamine B | Heptane | 75 | 21.5 | 0.38 |
| Rhodamine B | Gasoline | 71.5 | 13 | 0.21 |
| None | Heptane | 0 | 1 | — |
| None | Gasoline | 0 | 0.5 | — |
| Rhodamine 101 | Heptane | 73 | 20 | 0.35 |
| Rhodamine 101 | Gasoline | 73.5 | 12.5 | 0.20 |
| None | Heptane | 0 | 1.5 | — |
| None | Gasoline | 0 | 12.5 | — |
| Fluorescein | Heptane | 93.5 | 91 | 22.38 |
| Fluorescein | Gasoline | 97 | 101 | 10.41 |

Note:
the partition ratio (corrected for background) is calculated as follows: $K_D = [\text{Intensity Marker}]_{water}/[\text{Intensity Marker}]_{hydrocarbon}$ and an example calculation for Rhodamine B in Heptane is (21.5-1)/(75-(21.5-1)))

The ability to detect the marker compound in the water phase depends on a number of variables that may include the partition ratio, marker compound, and amounts of marker compound in the fuel. The intensity in the water phase after extraction (and thus the ability to detect the marker compound) tends to be proportional to the concentration of the marker in the fuel, intensity of the instrument's excitation wavelength, the sensitivity of the instrument's detector to the emission wavelength, the absorbance of the tracer to the excitation wavelength, and/or the fluorescence quantum yield as well as the water/gasoline partition ratio.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a range from 1 to 4 also means a range from 1 to 3, 1 to 2, 2 to 4, 2 to 3, and so forth.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A method for identifying a hydrocarbon fuel, the method comprising:
    obtaining a sample of a hydrocarbon fuel containing a measurable amount of a marker compound, the marker compound having a fluorescence intensity and at least partially soluble in distilled or deionized water;
    combining the hydrocarbon fuel with distilled or deionized water to form a fuel-and-water mixture and mixing the fuel-and-water mixture;
    after the mixing, allowing the fuel-and-water mixture to separate into a water phase and a fuel phase to at least partially extract the marker compound into the water phase;
    subjecting the water phase to light having a wavelength of 250 nm to 800 nm and observing the fluorescence emitted from the marker compound in the water phase; and wherein the marker compound having a fluorescence intensity has a structure of Formula II:

(Formula II)

2. The method of claim 1, wherein the observing step comprises measuring a fluorescence intensity of the water phase and determining the concentration of the marker compound in the hydrocarbon fuel based on the fluorescence intensity of the water phase with the at least partially extracted marker compound therein relative to a baseline fluorescence intensity of the water phase without the marker compound.

3. The method of claim 1, wherein the hydrocarbon fuel is selected from gasoline or diesel.

4. The method of claim 1, wherein the hydrocarbon fuel is gasoline containing ethanol.

5. The method of claim 4, wherein the gasoline contains at least about 2 volume percent ethanol.

6. The method of claim 1, wherein the hydrocarbon fuel includes a fuel performance additive selected from the group consisting of detergents, antioxidants, carrier fluids, metal deactivators, corrosion inhibitors, biocides, antistatic additives, drag reducing agents, demulsifiers, emulsifiers, dehazers, anti-icing additives, antiknock additives, anti-valve-seat recession additives, lubricity additives, surfactants, combustion improvers, or combinations thereof.

7. The method of claim 6, wherein the detergents are selected from the group consisting of Mannich reaction products formed by condensing a long-chain aliphatic hydrocarbon-substituted phenol or cresol with an aldehyde and an amine; long chain aliphatic hydrocarbons having an amine or a polyamine attached thereto; fuel-soluble nitrogen containing salts, amides, imides, succinimides, imidazolines, esters, and long chain aliphatic hydrocarbon-substituted dicarboxylic acids or their anhydrides or mixtures thereof; polyetheramines; and combinations thereof.

8. The method of claim 6, wherein the marker compound is added to the fuel performance additive.

9. The method of claim 1, wherein a relationship between fluorescence intensity of the water phase and the concentration of marker compound in the hydrocarbon fuel is linear.

10. The method of claim 9, wherein the hydrocarbon fuel includes about 0.1 to about 100 parts per billion of the marker compound.

11. The method of claim 1, wherein a partition ratio of the marker compound between the water phase and the fuel phase is at least about 0.1.

12. A method for identifying a hydrocarbon fuel, the method comprising:
obtaining a sample of a hydrocarbon fuel containing a measurable amount of a fluorescent marker, the fluorescent marker having a fluorescence intensity and at least partially soluble in water;
combining the hydrocarbon fuel with water to form a fuel-and-water mixture and mixing the fuel-and-water mixture;
after the mixing, allowing the fuel-and-water mixture to separate into a water phase and a fuel phase to at least partially extract the fluorescent marker into the water phase;
subjecting the water phase to light having a wavelength of 250 nm to 800 nm and observing the fluorescence emitted from the fluorescent marker in the water phase; and
wherein the fluorescent marker having a fluorescence intensity includes a compound having a structure of Formula III:

(Formula III)

wherein each $R_4$ is independently a C1 to C10 alkyl group.

13. The method of claim 12, wherein the observing step comprises measuring a fluorescence intensity of the water phase and determining the concentration of the fluorescent marker in the hydrocarbon fuel based on the fluorescence intensity of the water phase with the at least partially extracted fluorescent marker therein relative to a baseline fluorescence intensity of the water phase without the fluorescent marker.

14. The method of claim 12, wherein the hydrocarbon fuel is selected from gasoline or diesel.

15. The method of claim 12, wherein the hydrocarbon fuel is gasoline containing ethanol.

16. The method of claim 15, wherein the gasoline contains at least about 2 volume percent ethanol.

17. The method of claim 12, wherein the hydrocarbon fuel includes a fuel performance additive selected from the group consisting of detergents, antioxidants, carrier fluids, metal deactivators, corrosion inhibitors, biocides, antistatic additives, drag reducing agents, demulsifiers, emulsifiers, dehazers, anti-icing additives, antiknock additives, anti-valve-seat recession additives, lubricity additives, surfactants, combustion improvers, or combinations thereof.

18. The method of claim 17, wherein the detergents are selected from the group consisting of Mannich reaction products formed by condensing a long-chain aliphatic hydrocarbon-substituted phenol or cresol with an aldehyde and an amine; long chain aliphatic hydrocarbons having an amine or a polyamine attached thereto; fuel-soluble nitrogen containing salts, amides, imides, succinimides, imidazolines, esters, and long chain aliphatic hydrocarbon-substituted dicarboxylic acids or their anhydrides or mixtures thereof; polyetheramines; and combinations thereof.

19. The method of claim 12, wherein a relationship between the fluorescence intensity of the water phase and the concentration of fluorescent marker in the hydrocarbon fuel is linear.

20. The method of claim 19, wherein the hydrocarbon fuel includes about 0.1 to about 100 parts per billion of the fluorescent marker.

21. The method of claim 12, wherein a partition ratio of the fluorescent marker between the water phase and the fuel phase is at least about 0.1.

* * * * *